United States Patent [19]

Rodriquez

[11] Patent Number: 4,955,880
[45] Date of Patent: Sep. 11, 1990

[54] REUSABLE DIAPER PANT WITH DISPOSABLE LINER

[76] Inventor: Renee L. Rodriquez, N. 11604 Howard Ct., Spokane, Wash. 99218

[21] Appl. No.: 314,785

[22] Filed: Feb. 24, 1989

[51] Int. Cl.⁵ .............................................. A61F 13/15
[52] U.S. Cl. .................................................... 604/393
[58] Field of Search ........ 604/386, 387, 389, 393–397; 2/406, 407, 408; 24/573, 713.6

[56] References Cited

U.S. PATENT DOCUMENTS

| | | | |
|---|---|---|---|
| 2,575,165 | 11/1951 | Donovan | 604/401 |
| 2,606,558 | 8/1952 | Kennette | 604/399 |
| 3,407,813 | 10/1968 | Grippo et al. | 604/398 |
| 4,605,404 | 8/1986 | Sneider | 604/389 |
| 4,615,695 | 10/1986 | Cooper | 604/394 |

*Primary Examiner*—David J. Isabella
*Attorney, Agent, or Firm*—Wells, St. John & Roberts

[57] ABSTRACT

A diaper comprised of two parts, a reusable impervious pant and a disposable liner. The pant includes a folded pocket with snaps at both ends in the pocket to hold the liner, and snaps at all four corners to attach the pant around an infant. The liner includes a disposable pad with tape on back to secure to pants and has three holes at each end to slip over male portion of snaps in pocket and secure with female part. The liner is to be removed when soiled and a new liner can then be inserted. The waistband is padded and folded inwardly over the edge of the liner to provide cushioning, thereby protecting an infant from physical injury due to contact with the snaps.

2 Claims, 2 Drawing Sheets

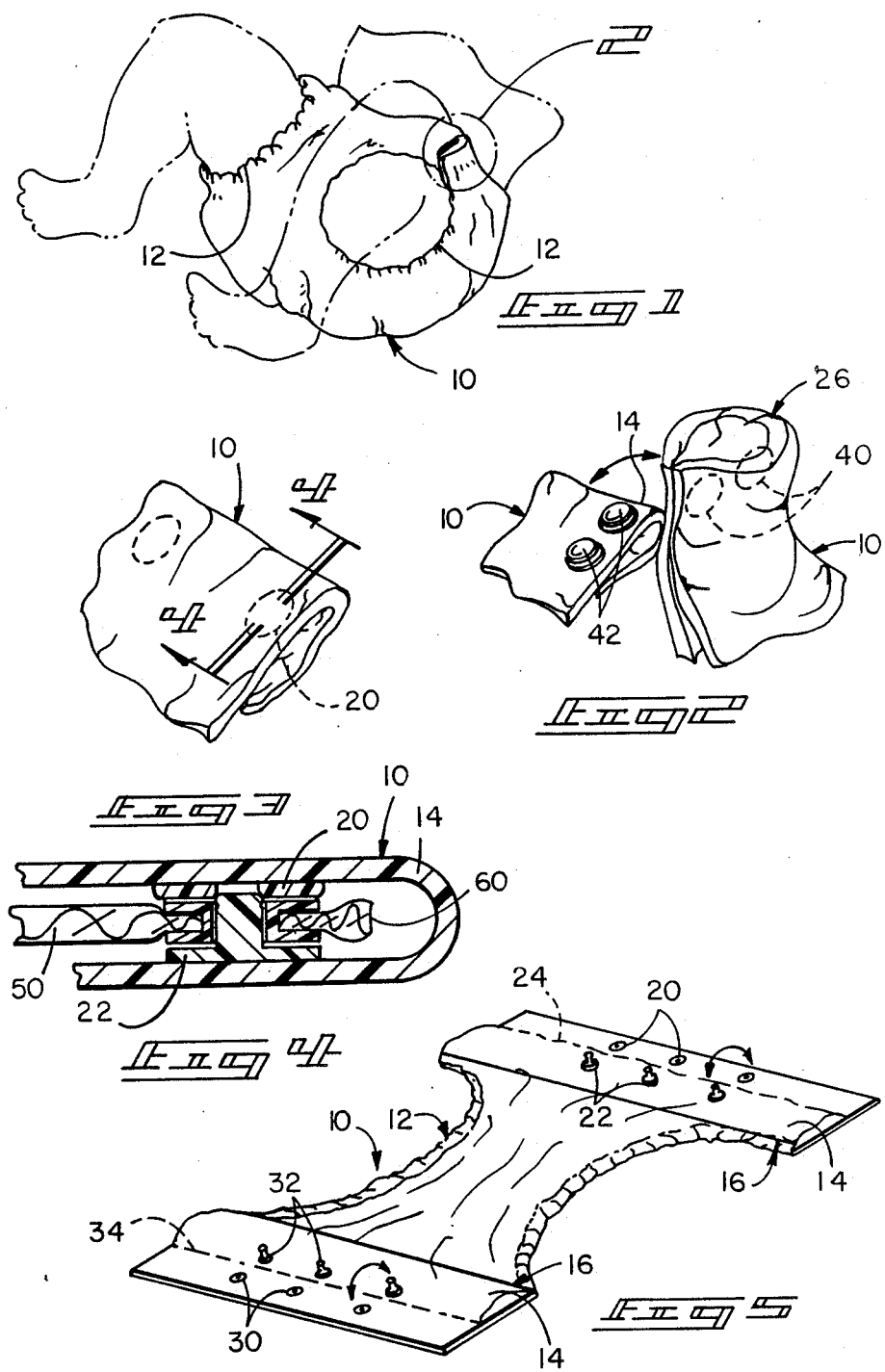

REUSABLE DIAPER PANT WITH DISPOSABLE LINER

BACKGROUND OF THE INVENTION

The present invention is a diaper in which the liner is disposable and the impervious pant is reusable. The diaper was designed to cost less than present disposable diapers in which the liner and impervious pant are attached, thus both disposable. It also is more ecologically sound because present disposable pants are difficult to decompose.

PRIOR ART

U.S. Pat. No. 2,606,558, issued to H. 0. Kennette, discloses a baby pant (10) with a disposable releasably attached liner (31). The liner is fastened by paired opposed snaps (12) at each end that releasably attach to the end portions of the pad by means of snaps. You will will note that the waistband portion of the pant garment is formed by a seam structure that apparently is somewhat thickened but that structure does not fold back upon itself as it is in the present invention. In general, the reference is relevant to show a releasable and replaceable absorbant pad in an impervious baby pant structure.

0. Hearlen, U.S. Pat. No. 3,900,032, shows another disposable pad and a holder for use of infants. In this case, the holder structure, as shown particularly in FIG. 3, folds back upon itself in the same fashion as the waistband of the present invention. A removable pad is positionable in the holder structure, but the pad is of a specialized nature having flexible fabric ties extending from its end portions so that those ties may be laced through the holes defined in the cover to reasonably positionably maintain the pad in the cover structure. This reference discloses the concept of forming a waistband by folding a portion of the waistband structure back upon itself, but it does not show the snap fastening means in the waistband and holes in the pad as the present invention for releasably maintaining the pad in position. position. It is hard to see exactly why this patent would fold the waistband back upon itself as there would be little purpose in so doing since cloth ties are used, whereas in the present invention there is purpose because the snaps might cause harm to an infant.

M. Donavan, U.S. Pat. No. 2,575,165, shows another baby diaper cover for a reusable pad structure. This reference again shows the waistband portion (31) that folds upon itself. The reference was cited principally for this purpose. The releasable pad of the structure is not too well illustrated, but apparently is long enough, as indicated in the specification, to extend into the folded over portion so that that portion aids in holding the pad in place. It does not appear, however, that the pad is positionally maintained by any type of releasable fastener such as the snaps of the present invention. It does appear, as indicated in the underlined portion of the reference at the bottom of column 6, however, that the folded over portion is to provide baby comfort which would be a purpose fairly similar to that of the folded waistband of the present invention.

P. G. Siegel, et al., U.S. No. Re. 23,853, shows another baby garment holding a disposable pad. This particular garment is not so relevant as the other references since it includes a top structure, though the bottom structure is essentially similar to the pant-like element of the present invention. The releasable diaper, however, is again not secured by a plurality of snap-type fasteners as in the present invention, and this reference would therefore not show that feature.

P. M. Rogatz, U.S. Pat. No. 2,544,726, shows another baby pant structure with a removable pad in the nature of a diaper. This particular pad has a snap fastening means (22) that would be somewhat similar to the present invention, but the fastening is not accomplished in the waistband itself and that waistband does not fold upon itself to cover the snap fastening means for the pad. This reference was cited principally to show the snap fastening means for a removable pad diaper.

P. G. Siegel, et al., U.S. Pat. No. 2,652,057, is very similar to the prior Siegel reissue patent and, in fact, uses the same drawings and describes substantially the same thing. The fastening means again are different, the fastening is not accomplished in the waistband portion, and the waistband only coincidentally shows a folded over part, but one that does not cover the snaps carried therein.

M. E. Margraf, U.S. Pat. No. 3,050,063, shows a pinless baby diaper. Apparently the main thrust of this invention is to provide a diaper that fastens without pins, but coincidentally in so doing, it discloses a basic pant-like structure with an inner removable pad-like element. Apparently from the specification, both halves of the device may be separately used. You will note the snap-like fastening structure, but again it does not appear to provide a folded over waistband, at least about all portions of the waistband of a diaper. The device would also be distinguishable in that it does not disclose a waterproof pant as such with an inner absorbant pad. The reference in general is not so relevant as the other references disclosed that deal with baby pants having removable pads as such.

G. Salk, U.S. Pat. No. 3,162,196, shows yet another baby pant with a removable pad structure. The illustrations of FIG. 3 seem to best show the device. You will note here that the use of snaps is disclosed to fasten the pad within the pant device, but the fastening is not accomplished in the waistband structure itself and the waistband's structure does not fold upon itself to create the waistband.

A. Pociluyko, U.S. Pat. No. 3,658,064, shows yet another supporting garment and disposable pad for a diaper-like device. Here you will note that one end of the waistband has a portion that folds upon itself to form a padded waistband and it also discloses snap-type fasteners to hold the folded members in appropriate position. The pad, however, is not fastened by snap-type fasteners and is not fastened in the waistband structure, but rather with auxiliary flaps that do not appear in the present art.

P. Jarvsik, et al., U.S. Pat. No. 3,693,621, again shows a baby pant structure with a removable pad. The main thrust of the patent seems to be concerned more with the particular holding device (60), but you will note that the pad folds upon itself in the structure. Undoubtedly this reference is no closer, if as close, as the other prior references for the same reasons before set forth.

P. Gamm, et al., U.S. Pat. No. 3,828,785, shows another pant-like garment with an elongated absorbant pad for use on incontinence. The pad is somewhat different in shape than that of the present device and appears to be more of an elongated tube, but it is disclosed as being releasably fastenable within the pant-like garment. Snap fasteners are used in the waistband structure to fasten the ends of the tubular absorbent pad in the pant garment. There is no disclosure, again, however, of the waistband being formed in a folded-over fashion as such and there is no showing of the fastening of the ends of the absorbant pad in such a folded over waistband.

P. Caradonna, U.S. Pat. No. 4,244,368, shows yet another incontinent garment having a pant-like portion and a releasably attachable pad. Here, the liner devices have snap-like structures in the waistband of the device. This garment, again, does not seem to be much different that the others cited and is distinguishable from any invention in that it does not show a waistband that show a waistband that folds upon itself to fasten the ends of the releasable pad within the waistband structure.

OBJECT OF THE INVENTION

It is therefore the object of this invention to create a two-part diaper consisting of a reusable impervious pant, able to hold a disposable liner.

A further objective is to protect the baby from physical injury from the snaps by use of a padded and folded waistband.

A further objective is to create a disposable diaper secured in place by both snaps and tape.

A further objective is to create a disposable diaper in which neither portion of the snap needs to be fastened to the pad itself saving money and time in production.

It would appear that all of the art cited shows some sort of a pant-like garment with a releasably fastenable and removable pad of one sort or another that is for use either upon infants or incontinent persons. Each of the individual features of the invention, per se, are shown separately, though not in combination in any of the references. Snap fasteners for releasably fastening such pads are shown at least by Kennette, Rogatz, Margraf, Salk, and Gamm. Fold-over type waistbands of one sort or another and for all or part of the waistband structure are shown at least by Donovan, Margraf, Pociluyko, and Jarusik.

None of the previous patents, however, show snap-type fasteners that are used to fit in holes at the ends of the pad and are contained in the folded-over seam. Obviously, then, this feature would be something new and different over the prior art.

BRIEF DESCRIPTION OF THE DRAWINGS

FIG. 1 is a view of an infant wearing one of the garments of this invention.

FIG. 2 is an enlarged view of the snaps placement that holds the diaper on the infant.

FIG. 3 is an enlarged front view of the snaps in FIGS. 4 and 7, holding the removable diaper onto the reusable pant.

FIG. 4 is a closeup sideview of FIG. 3 displaying the male and female parts of the snap holding the disposable liner in place.

FIG. 5 is an unfolded perspective view of the reusable outer pant.

DETAILED DESCRIPTION

Figure 6:
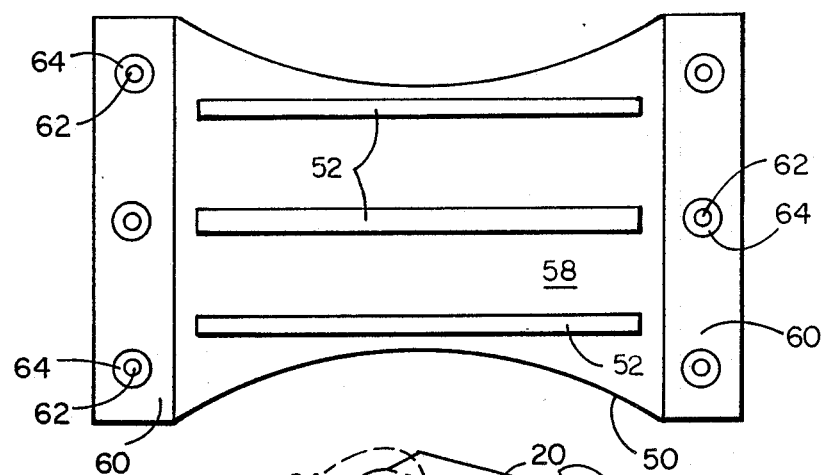
FIG. 6 is a plain view of the removable disposable liner.

FIG. 1 shows the assembled diaper, as it fits onto the body, with (12), the elasticized leg opening, and the impervious pant on the outside.

FIG. 2 shows a detailed drawing of the closure snaps, (40) and (42). Number (42), the female snap, protrudes only through the top fold, so the rear of the snap does not touch the body. Number (42) is also placed through the outside fold only, so its rear portion is not attached to the outside of the impervious pant. The impervious pant folds at both ends. Both folds have padding, (14) underneath the snaps.

FIG. 3 shows the enlarged side version of the snaps, (20) and (22), after folding on top of the disposable liner.

FIG. 4 shows a side closeup view of the liner (10), folded over itself, enclosing the batting (14). The top fold with its female snaps, (20) and (30), meets the bottom fold with the male snaps, (22) and (32) securing the disposable liner (50) in its pre-punched holes, (62) and (64) in the edge of the liner.

FIG. 5 shows the unfolded impervious pant (10), before the disposable liner is put in place. The batting (14) is held in place against the impervious pant, by a stitched seam at (16). The upper and lower edges holding the female snaps (20) and (30) fold onto the male snaps (22) and (32), at lines (24) and (34). The leg area is gathered with elastic (12).

FIG. 6 is a reverse view of the disposable liner (58) showing the adhesive material strips (52) which temporarily secure the liner to the impervious pant. The liner ends (60) have pre-cut holes (62), strengthened by circular reinforcement tape (64). The liner ends (60) are made of a non-absorbent, non-bulky material. The liner body (50) is made of absorbent material.

Figure 7:
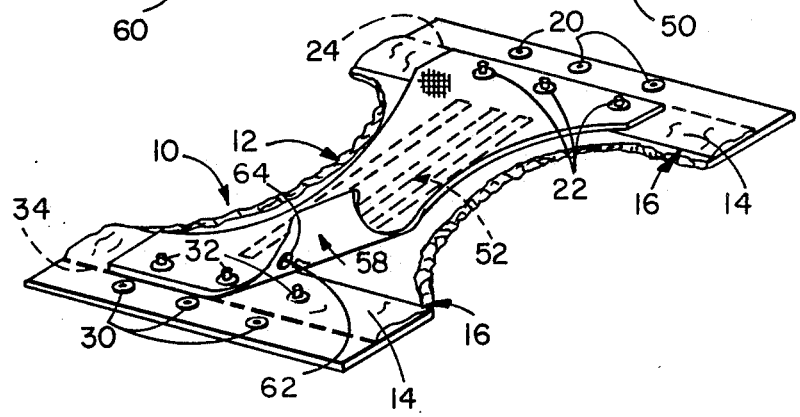
FIG. 7 is a detailed perspective view of how the disposable liner is put in place inside the permanent pant.

FIG. 7 shows the disposable liner (58) being put into place inside the impervious pant (10), before the snaps are secured at (20-22) and (30-32).

Figure 8:
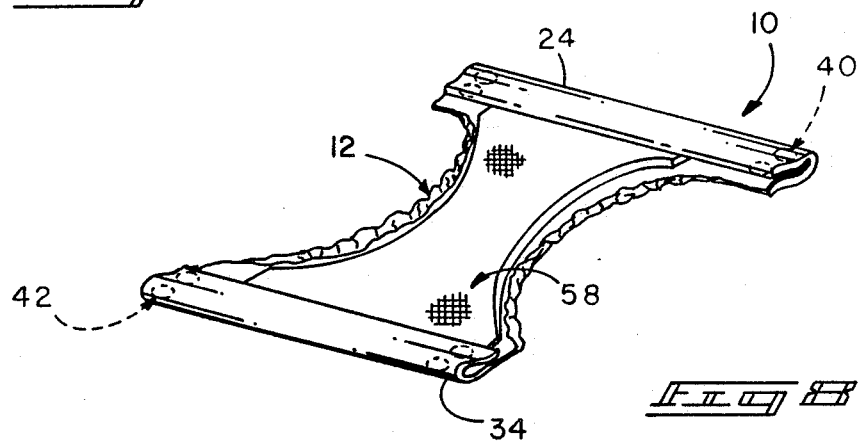
FIG. 8 is a perspective view of a finished assembly of both the disposable liner and reusable pant ready to place on an infant.

FIG. 8 shows the assembled diaper. The disposable liner is secured inside the folds of impervious pant, both by snaps and by adhesive strips.

The embodiments of the invention in which particular property or privilege is claimed are defined as follows:

1. A diaper, comprising:
   am impervious pant in the form of a sheet having elasticized leg side edges extending between opposed waistband ends and including opposed inside and outside surfaces extending along its complete length;
   the waistband ends each including a fold extending across the pant between its leg side edges, each fold including an outer section and an inner section separated from the outer section by a fold line;
   female snap members on the inside surface of the sheet at one of the inner or outer sections at each of the opposed waistband ends;
   male snap members on the inside surface of the pant at the remaining one of the inner or outer sections at each of the opposed waistband ends for engagement with the female snap members;
   an elongated absorbent liner having side edges extending between opposed transverse ends, each transverse end of the liner having openings formed through it for receiving the male snap members on the pant;

the liner including adhesive means along one surface for securing the liner to the inside surface of the pant;

whereby the outer sections of the pant are foldable over its inner sections to completely cover and sandwich the transverse ends of the liner between them with the female and male snap members engaging one another through the openings in the liner and with the engaged snap members covered by the folded outer and inner sections of the pant.

2. A diaper, comprising:

an impervious pant in the form of a sheet having elasticized leg side edges extending between opposed waistband ends and including opposed inside and outside surfaces extending along its complete length;

the waistband ends each including a fold extending across the pant between its leg side edges, each fold including an outer section and an inner section separated from the outer section by a fold line;

female snap members on the inside surface of the sheet at one of the inner or outer sections at each of the opposed waistband ends;

male snap members on the inside surface of the pant at the remaining one of the inner or outer sections at each of the opposed waistband ends for engagement with the female snap members;

an elongated absorbent liner having side edges extending between opposed transverse ends, each transverse end of the liner having openings formed through it for receiving the male snap members on the pant;

the liner including non-absorbent transverse ends and the openings formed through the liner being reinforced about their respective peripheries;

whereby the outer sections of the pant are foldable over its inner sections to completely cover and sandwich the transverse ends of the liner between them with the female and male snap members engaging one another through the openings in the liner and with the engaged snap members covered by the folded outer and inner sections of the pant.

* * * * *